United States Patent [19]

Alexander

[11] Patent Number: 5,843,477
[45] Date of Patent: Dec. 1, 1998

[54] LUBRICANTS FOR USE IN TABLETTING

[75] Inventor: Thomas A. Alexander, Granger, Ind.

[73] Assignee: Bayer Corporation, Pittsburgh, Pa.

[21] Appl. No.: 941,086

[22] Filed: Sep. 30, 1997

[51] Int. Cl.⁶ .................. A61K 9/46; A61K 9/20
[52] U.S. Cl. .................. 424/466; 424/465; 424/489; 424/464
[58] Field of Search .................. 424/464, 465, 424/466, 489

[56] References Cited

U.S. PATENT DOCUMENTS

| | | |
|---|---|---|
| 4,783,331 | 11/1988 | Alexander et al. . |
| 4,965,072 | 10/1990 | Alexander et al. . |
| 5,445,827 | 8/1995 | Fritsch et al. . |
| 5,587,179 | 12/1996 | Gergely et al. . |
| 5,639,475 | 6/1997 | Bettman et al. . |
| 5,650,169 | 7/1997 | Conte et al. . |
| 5,681,583 | 10/1997 | Conte et al. . |
| 5,709,886 | 1/1998 | Bettman et al. . |
| 5,728,401 | 3/1998 | Ahmed et al. . |

*Primary Examiner*—Thurman K. Page
*Assistant Examiner*—Brian K. Seidleck
*Attorney, Agent, or Firm*—Burns, Doane, Swecker & Mathis, L.L.P.

[57] ABSTRACT

The invention provides a new water soluble lubricant combination which facilitates the production of tablets. The combination of glyceryl behenate and fumaric acid is useful as a lubricant, particularly in tablet compositions containing ingredients where rapid dissolution in an aqueous environment is desired for activity or desired for aesthetic purposes. This lubricant combination has fewer limitations and improved functionality in comparison to standard lubricants presently known. In addition, the lubricants provided may be used with known hydrophobic lubricants to decrease the amount of the hydrophobic lubricant required for lubrication.

8 Claims, No Drawings

LUBRICANTS FOR USE IN TABLETTING

BACKGROUND OF THE INVENTION

1. Field of the Invention

The invention relates to lubricants used in tabletting. In particular, the invention relates to lubricants used in the tabletting of water soluble tablets or effervescent tablets.

2. Description of the Related Art

In order to compress a composition into tablets, lubrication of the tabletting machinery is generally required. Although it is possible to lubricate the dies and presses directly (external lubrication), the problems involved when tablets are to be prepared commercially at a high speed makes their use impractical. Therefore, most lubricants used are added to the formulation itself (internal lubrication). When a lubricant is added to the formulation, it must provide the necessary lubrication without interfering with the flowability or compressibility of the formulation and without interfering with the release of the active ingredient. Many of the best lubricants are hydrophobic or water insoluble, for example, calcium or magnesium stearate, talc, and vegetable oils; and for many formulations where rapid release of the active ingredient is not required, these lubricants are sufficient.

Lubrication of tablets where rapid dissolution is desired, however, presents a particular problem since hydrophobic lubricants may impede the release of the active ingredient(s) from the tablet. When the tablet is a pharmaceutical, the release of the active ingredient may be crucial to the onset of action and even to whether the ingredient elicits the desired response. In addition, when a tablet which is intended for dissolution in water prior to ingestion is prepared, e.g. an effervescent tablet, hydrophobic lubricants are generally avoided because their presence tends to leave an unsightly scum upon dissolution making the solution less palatable and aesthetically pleasing to the consumer.

Water soluble lubricants do not impede the release of active ingredient(s) from the tablet like that of hydrophobic lubricants. However, water soluble lubricants generally have poorer lubrication properties than the hydrophobic lubricants. Therefore, there has been a proliferation of compositions and processes providing soluble lubricants. Known soluble lubricants include: fumaric acid, adipic acid, boric acid, sodium benzoate, potassium benzoate, sodium propionate, sodium stearyl fumarate, sodium lauryl sulfate, magnesium lauryl sulfate, L-leucine and various polyethylene glycols ranging in (average) molecular weight from 4000 to 20000. There have been a number of patents related to lubricants for tabletting pharmaceuticals or nutritional supplement, including, for example, U.S. Pat. Nos. 3,566,491; 3,548,099; 3,518,346; 3,506,756; 3,518,343; 3,518,344; 3,518,345; 3,619,462; 3,577,490; and 3,577,492. In particular, there have been a number of patents related to the use of fumaric acid as a lubricant for tabletting pharmaceuticals or nutritional supplements, including, for example, U.S. Pat. Nos. 3,518,346; 3,577,490; and 3,577,491.

These known lubricants, however, still have significant limitations. Therefore, a need continues to exist for water soluble lubricants which may be used in general, but in particular for tabletting fast dissolving pharmaceuticals and/or nutritional supplements.

SUMMARY OF THE INVENTION

It has been found that the combination of glyceryl behenate and fumaric acid in levels lower than traditionally used may be used as a sole tablet lubricant in a tablet composition. A relatively low proportion of glyceryl behenate, from about 0.15% to 0.35% per tablet, can be used with approximately 1.0% to 2.0% per tablet of fumaric acid. More preferably, approximately 0.2% per tablet of glyceryl behenate can be used with about 1.6% per tablet of fumaric acid. Another preferable embodiment is that the fumaric acid is micronized. This combination lubricant provides the practitioner with a significant improvement in available lubricants for compressed tablets and is useful for a wide range of tablet compositions.

DETAILED DESCRIPTION OF THE INVENTION

The new lubricants and lubricant formulations of this invention are particularly important for tablet compositions intended for dissolution in water such as effervescent tablets and to tablet compositions, such as pharmaceuticals and/or nutritional supplements, from which the active ingredient should be released quickly into a body fluid in order to be adsorbed and to exhibit activity. Effervescent tablets, which are commonly dissolved in water prior to ingestion, should dissolve without residue or film formation, both for aesthetic reasons and to avoid trapping the active ingredient in the residue or film. Such trapping may result in the delivery of less active ingredients than are expected. Swallow or "regular" or "standard" tablets are commonly intended to be swallowed whole, and with subsequent disintegration and absorption from a body fluid, to deliver the active ingredient. In most cases such tablets preferably disintegrate rapidly thereby providing a large surface area from which the active ingredient dissolves into the body fluid. If a hydrophobic lubricant is used, those of skill in the art take care that the lubricant does not coat the composition particles prior to compression, which coating could make the particles generally hydrophobic and impede the release of the active ingredient(s). Such care may require special handling of the composition, usually by controlling the addition sequence and shortening time the lubricant is mixed with the rest of the ingredients. In contrast, the sole lubricants of this invention may be added directly to and mixed with the remaining ingredients, decreasing the number of steps required to prepare a formulation for tabletting. Although the new lubricants and lubricant formulations (the term "lubricants" is used generally herein to refer to both sole lubricants and lubricant formulations) are particularly applicable to tablet compositions requiring dissolution prior to use, the lubricants provided may also be used when unimpeded water solubility is not required.

Active Ingredients

The lubricants may generally be used with any active ingredient requiring tabletting, absent some chemical incompatibility. Effervescent formulations commonly contain analgesics, antacids, decongestants, antihistamines and/or expectorants. In addition, the whole gamut of pharmaceuticals may be tabletted with the lubricants provided, including but not limited to, those listed above, H2 blockers, antibiotics, sedatives, hypnotics and migraine preparations. Nutritional supplements such as vitamins and minerals, herbals and other dietary supplements may also be tabletted with these lubricants. Many of these ingredients are water soluble and therefore the lubricants provided have particular advantages.

Other Ingredients

In addition to the active ingredient(s), other tabletting ingredients, well known to those of skill in the art may be used as needed. All such ingredients in pharmaceuticals and nutritionals must support the tablet function of delivering and releasing the active ingredient(s) to the body in the intended manner. These other ingredients commonly include colors, flavors, diluents, binders, fillers and disintegrants. For effervescent tablets, all such ingredients should be water soluble.

Lubricants

Lubricants are generally chosen by balancing the need for lubrication of the composition during tabletting with the need to find a lubricant which does not impede the release and/or availability of the active ingredients. The lubricants or lubricant combination provided may be used as the sole lubricant, or may be used in combination with other lubricants well known to those of skill in the art of compressed tabletting. They may be advantageously used in combination with water insoluble lubricants. Such water insoluble lubricants generally provide the best tablet lubrication, but because of the problems of dissolution and drug release, must be used in the smallest amount possible. The combination lubricant provided herein with insoluble, hydrophobic lubricants, allows the amount of the hydrophobic lubricant to be decreased.

Lubricant concentrations are given as a weight percent of tablet composition. This is generally the minimum amount which has been shown to provide useful lubrication. However, lower amounts of about 0.5 weight percent less may be used and higher amounts may be used up to the point at which the lubricant interferes with either the tabletting or with the disintegration and release of the active ingredient. Given the disclosure and examples provided herein, those of skill in the art will be able to use the lubricants provided, advantageously, for a wide range of tablet formulations particularly for pharmaceutical and nutritional supplements.

Glyceryl Behenate

Glyceryl behenate has been used as a lubricant for standard tablets. In general, it has been found that it provides lubrication at about 1.5–3.0% (Vendor literature) by weight of the tablet composition. However, glyceryl behenate was not previously known to be used in water soluble or effervescent tablets. The present inventor has now found that glyceryl behenate can act as a water soluble lubricant which has both antiadherent and antifrictional lubricant properties and therefore may be used as the sole lubricant. In addition, it may be used in combinations provided herein as lubricant formulations. It may also be used with standard lubricants known to those of skill in the art, for example, magnesium stearate. The present inventor has further discovered that when glyceryl behenate is used in combination with fumaric acid, the amount of glyceryl behenate and fumaric acid may be decreased.

Fumaric Acid

Fumaric Acid has been used as a water soluble lubricant alone previously and in other combinations. In general, is has been found that it provides lubrication at about 3–5% by weight of the tablet composition. In addition, it may be used in combinations provided herein as lubricant formulations. It may also be used with standard lubricants known to those of skill in the art. However, the present inventor has discovered that when fumaric acid is used in combination with glyceryl behenate, the amount of fumaric acid and glyceryl behenate may be decreased.

Glyceryl Behenate/Fumaric Acid Combination

While tabletted ingredients are commonly granular and have a coarse particle size to impart good flow properties to the composition, lubricants in general, including the lubricants calcium and potassium sorbate and the other lubricant formulations provided herein, are preferably added to the remaining tablet composition in a form having a very fine particle size. This can be accomplished in a variety of ways well known to those of skill in the art.

Micronization of Fumaric Acid

The fumaric acid may be prepared in a fluid energy mill, (also called an air mill or a micronizer) in which particle size reduction is accomplished through high speed impact of feed material particles with each other as they are carried through the mill by a high velocity gas stream. The impact causes a shattering of hard materials and a smearing of soft materials. The desired particle size is less than 10 microns.

Use of the Lubricant Combination

The use of the lubricants and lubricants formulations provided here is specifically illustrated in the Example which illustrates their use in effervescent formulations, which have particular tabletting lubrication problems due to the requirement of fast, complete dissolution in water prior to ingestion. Given the guidance in this specification and particularly in the Example, one of ordinary skill in the art of tabletting compression will be able to use the lubricants and lubricant formulations provided in any number of tablet compositions requiring lubrication.

In general an effervescent tablet may be prepared by mixing a effervescent couple (an edible organic acid and an alkaline metal salt of a carbonate, bicarbonate or an acid anhydride) with one of the lubricants or lubricant formulations provided herein, blending and compressing the mixture into tablets. A common effervescent couple is composed of citric acid and sodium bicarbonate. When a stoichiometric excess of bicarbonate is used the formulation will function, after ingestion in water solution, as an antacid. A high neutralizing capacity as indicated by testing according to USP XXII for an antacid may be easily achieved in this manner. There are many effervescent formulations well known to those of skill in the art of effervescent tabletting which may be improved with the lubricants and lubricant formulations provided herein.

Swallow tablets (i.e., tablets designed for ingestion, whole—sometimes known as swallowable tablets and often thought of as regular tablets) may also be advantageously prepared with the lubricants provided herein. Commonly the tablet ingredients may be prepared in a granulation and the lubricant and additional components such as a tablet disintegrant like crospovidone or cornstarch, or a tablet binder like silicon dioxide or alpha cellulose are blended and compressed by standard methods well known to those of skill in the art without special handling.

The following Example discloses a preferred embodiment of the invention, but does not limit the applicability of the invention which is solely defined by the claims.

EXAMPLE

Glyceryl behenate/fumaric acid lubrication of an Effervescent Formulation

Micronized fumaric acid 35 mg/tablet and 4.5 mg/tablet glyceryl behenate were passed through a 24 mesh stainless steel wire mesh screen immediately prior to use. The glyceryl behenate was supplied by Gattfosse Corporation, Elmsford, N.Y. as Compritol 888. The remaining components, in granular form, and the screened lubricants were mixed together in a 1 cu. ft. dry twinshell blender. The powder was compressed on a Kilian RT-1 16 tablet press at a constant speed of 30 rpm. The tablet tooling was ⅞ inch round flat face bevel edge and a ⅞ inch die with a ⅝ inch taper and micro-finish coating. The compression force was varied from about 1800 kg to 6400 kg.

Generally between 0.15% to 0.35% of glyceryl behenate could be used with fumaric acid with no significant effect on mixing times or press speeds. Within this range, it was possible to obtain optimal harness and dissolution with optimal ejection and compression forces.

It should be understood that many modifications and variations can be made in the proportions and components used herein without departing from the spirit and scope of the invention, which is solely defined by the claims.

What is claimed is:

1. A method of preparing a tablet, comprising the steps of:
    a. preparing the lubricant combination of glyceryl behenate and micronized fumaric acid;
    b. adding the lubricant combination and the desired tablet ingredients to a mixer;
    c. blending the contents of the mixer;
    d. compressing the blended contents to produce a tablet.

2. The method of claim 1, wherein said glyceryl behenate is present in the amount of about 0.15% to 0.35% per tablet.

3. The method of claim 1, wherein said micronized fumaric acid is present in the amount of about 1.0% to 2.0% per tablet.

4. The method of claim 1, wherein said tablet is effervescent.

5. A tablet prepared by the method according to claim 1.

6. The tablet of claim 5, wherein said glyceryl behenate is present in an amount of about 0.15% to 0.35% per tablet.

7. The tablet of claim 5, wherein said micronized fumaric acid is present in an amount of about 1.0% to 2.0% per tablet.

8. The tablet of claim 5, wherein said tablet is effervescent.

* * * * *